(12) United States Patent
Du et al.

(10) Patent No.: US 12,178,635 B2
(45) Date of Patent: Dec. 31, 2024

(54) ULTRASONIC IMAGING SYSTEM AND BLOOD FLOW IMAGING METHOD

(71) Applicant: SHENZHEN MINDRAY BIO-MEDICAL ELECTRONICS CO., LTD., Guangdong (CN)

(72) Inventors: Yigang Du, Shenzhen (CN); Yongqiang Dong, Shenzhen (CN); Wei Fan, Shenzhen (CN); Lanxi Xiang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 533 days.

(21) Appl. No.: 17/349,030

(22) Filed: Jun. 16, 2021

(65) Prior Publication Data

US 2021/0378626 A1    Dec. 9, 2021

Related U.S. Application Data

(63) Continuation of application No. PCT/CN2018/121707, filed on Dec. 18, 2018.

(51) Int. Cl.
*A61B 8/06*    (2006.01)
*A61B 8/00*    (2006.01)
(Continued)

(52) U.S. Cl.
CPC .......... *A61B 8/06* (2013.01); *A61B 8/14* (2013.01); *A61B 8/463* (2013.01); *G01S 7/5202* (2013.01);
(Continued)

(58) Field of Classification Search
None
See application file for complete search history.

(56) References Cited

U.S. PATENT DOCUMENTS

| 10,976,422 B2 | 4/2021 | Du et al. |
| 11,259,784 B2 | 3/2022 | Du et al. |

(Continued)

FOREIGN PATENT DOCUMENTS

| CN | 103181789 A | 7/2013 |
| CN | 105530870 A | 4/2016 |

(Continued)

OTHER PUBLICATIONS

Bottenus, Nick. "Comparison of virtual source synthetic aperture beamforming with an element-based model." The Journal of the Acoustical Society of America 143.5 (2018): 2801-2812. (Year: 2018).*

(Continued)

*Primary Examiner* — Serkan Akar
*Assistant Examiner* — Aminah Asghar
(74) *Attorney, Agent, or Firm* — Sheppard Mullin Richter & Hampton LLP

(57) ABSTRACT

An ultrasonic imaging system and an imaging method. The imaging method comprises: transmitting a divergent ultrasonic beam to a scanning object, and scanning the scanning object with the divergent ultrasonic beam (S11); a self-scanning object receiving an echo of the divergent ultrasonic beam, and obtaining divergent ultrasonic echo signals by means of beam synthesis (S12); obtaining blood flow velocity vector information of the scanning object according to the divergent ultrasonic echo signals (S13); and displaying the blood flow velocity vector information of the scanning object (S14). Using a divergent ultrasonic beam to perform blood flow imaging can ensure that there is a sufficiently large scanning area for covering a scanning object, thereby achieving ultrasonic blood flow imaging at a high frame rate.

15 Claims, 8 Drawing Sheets

(51) Int. Cl.
  *A61B 8/14* (2006.01)
  *G01S 7/52* (2006.01)
  *G01S 15/89* (2006.01)

(52) U.S. Cl.
  CPC ...... *G01S 7/52053* (2013.01); *G01S 15/8915* (2013.01)

(56) References Cited

U.S. PATENT DOCUMENTS

| | | |
|---|---|---|
| 2012/0265075 A1 | 10/2012 | Pedrizzetti et al. |
| 2013/0172745 A1 | 7/2013 | Choi |
| 2017/0071576 A1 | 3/2017 | Du et al. |
| 2018/0085088 A1 | 3/2018 | Du et al. |
| 2018/0146952 A1 | 5/2018 | Du et al. |
| 2020/0041644 A1* | 2/2020 | Brown ................ G01S 15/8927 |

FOREIGN PATENT DOCUMENTS

| | | | |
|---|---|---|---|
| CN | 106102587 A | 11/2016 | |
| CN | 106102589 A | 11/2016 | |
| WO | WO-2016119247 A1 * | 8/2016 | ............... A61B 8/00 |

OTHER PUBLICATIONS

PCT International Search Report and the Written Opinion mailed Sep. 18, 2019, issued in related International Application No. PCT/CN2018/121707, with partial English translation (11 pages).
PCT International Preliminary Report on Patentability mailed Jul. 1, 2021, issued in related International Application No. PCT/CN2018/121707, with English translation (13 pages).
First Search dated Mar. 18, 2022, issued in related Chinese Application No. 201880097327.1 (3 pages).

* cited by examiner

T₁ T₂ T₃ T₄ T₅ T₆ T₇ T₈ T₉ T₁₀ ······ T₂₀ first frame      second frame

_US 12,178,635 B2_

ULTRASONIC IMAGING SYSTEM AND BLOOD FLOW IMAGING METHOD

CROSS-REFERENCE TO RELATED PATENT APPLICATION

This application is a continuation of International Patent Application No. PCT/CN2018/121707, filed with the China National Intellectual Property Administration (CNIPA) on Dec. 18, 2018. The content of the above application is incorporated herein by reference in its entirety.

TECHNICAL FIELD

The present disclosure relates to medical ultrasound systems, in particularly to ultrasound imaging systems and blood flow imaging methods.

BACKGROUND OF THE INVENTION

In a traditional UCG (ultrasonic cardiography) examination on a person to be detected, due to the person's heart being blocked by the person's ribs, a probe may only be placed between two ribs, leading to a very narrow width scanned by the probe. Deflection emission is usually required for the probe to achieve sector scanning, thereby enlarging the scanning area, as shown in FIG. 1. For the technique of ultrasonic vector flow imaging based on multi-angle deflection emission, since a multi-angle defection emission is performed to a same region and velocity components of different angles in an overlapped region formed by the emission are calculated to synthesize a vector velocity, when applying this technology to examine heart and using a phase array probe for vector flow, the traditional plane waves of the multi-angle overlapped region may be reduced a lot. The overlapped region obtained by using the plane waves gradually shrinks in a direction away from the probe, as shown in FIG. 2; in this respect, a wider sector scanning cannot be achieved and it is difficult for the scanned region to cover the entire heart.

SUMMARY OF THE INVENTION

According to a first aspect of the present disclosure, an ultrasonic blood flow imaging method is provided, which may include:

transmitting first divergent ultrasound beams corresponding to a first virtual focus to a scan target at least twice, a to-be-scanned region of the scan target being covered by a first scanning area of the first divergent ultrasound beams; and transmitting second divergent ultrasound beams corresponding to a second virtual focus to the scan target at least twice, the to-be-scanned region of the scan target being covered by a second scanning area of the second divergent ultrasound beams;

receiving echoes of the first divergent ultrasound beams to obtain a group of first divergent ultrasonic echo signals that includes the first divergent ultrasonic echo signals received at least twice; and receiving echoes of the second divergent ultrasound beams to obtain a group of second divergent ultrasonic echo signals that includes the second divergent ultrasonic echo signals received at least twice;

calculating a first velocity component of the target point in the to-be-scanned region of the scan target in a first direction based on the group of the first divergent ultrasonic echo signals; and calculating a second velocity component of the target point in the to-be-scanned region of the scan target in a second direction based on the group of the second divergent ultrasonic echo signals;

generating blood flow velocity vector information of the target point in the to-be-scanned region based on the first velocity component and the second velocity component; and displaying the blood flow velocity vector information of the target point in the to-be-scanned region;

wherein the position of the first virtual focus is different from the position of the second virtual focus, the first scanning area and the second scanning area are at least partially overlapped, and the to-be-scanned region of the scan target is covered by the overlapped scanning area;

wherein a plurality of transducers of the probe are excited with a first group of transmission time delays to transmit ultrasonic waves to the scan target to form the first divergent ultrasound beams in a time-sharing manner, the ultrasonic waves transmitted by the transducers closer to the first virtual focus is transmitted earlier than the ultrasonic waves transmitted by the transducers far away from the first virtual focus in the first group of transmission time delays; and a plurality of transducers of the probe are excited with a second group of transmission time delays that is different from the first group of transmission time delays to transmit ultrasonic waves to the scan target to form the second divergent ultrasound beams in a time-sharing manner, the ultrasonic waves transmitted by the transducers closer to the second virtual focus is transmitted earlier than the ultrasonic waves transmitted by the transducers far away from the second virtual focus in the second group of transmission time delays.

According to a second aspect of the present disclosure, an ultrasonic blood flow imaging method is provided, which may include:

exciting a probe by a transmitting circuit to transmit divergent ultrasound beams to the to-be-scanned region of the scan target that is covered by the scanning area of the divergent ultrasound beams;

receiving echoes of the divergent ultrasound beams by the probe to obtain first electric signals, receiving the first electric signals by a receiving circuit, and performing beam synthesis on the first electric signals by a beam synthesis unit to obtain a group of divergent ultrasonic echo signals;

calculating the direction and magnitude of velocity of the target point in the to-be-scanned region of the scan target by a processor based on the group of divergent ultrasonic echo signals to generate blood flow velocity vector information of the target point in the to-be-scanned region; and displaying the blood flow velocity vector information of the target point in the to-be-scanned region on a display.

According to a third aspect of the present disclosure, an ultrasound imaging method is provided, which may include:

transmitting divergent ultrasound beams to a scan target multiple times and scanning the scan target with the divergent ultrasound beams;

receiving echoes of the divergent ultrasound beams from the scan target multiple times to obtain divergent ultrasonic echo signals;

generating the blood flow velocity vector information of the scan target based on the divergent ultrasonic echo signals; and displaying the blood flow velocity vector information of the scan target.

According to a fourth aspect of the present disclosure, an ultrasound imaging system is provided, which may include:

a probe, configured for transmitting divergent ultrasound beams and receiving echoes of divergent ultrasound beams to obtain first electric signals;

a transmitting circuit, configured for exciting the probe to transmit divergent ultrasound beams to a scan target so as to scan the scan target;

a receiving circuit and a beam synthesis unit, configured for receiving and processing the first electric signals to obtain divergent ultrasonic echo signals;

a processor, configured for obtaining blood flow velocity vector information of the scan target based on the divergent ultrasonic echo signals; and a display, configured for displaying the blood flow velocity vector information of the scan target.

BRIEF DESCRIPTION OF THE DRAWINGS

In order to explain the embodiments of the present disclosure or the technical solutions in the prior art more clearly, the following will briefly introduce the drawings that need to be used in the description of the embodiments or the prior art. Obviously, the drawings in the following description are only some embodiments of the present disclosure. For those skilled in the art, other drawings can be obtained based on these drawings without creative labor.

DETAILED DESCRIPTION

Figure 3:
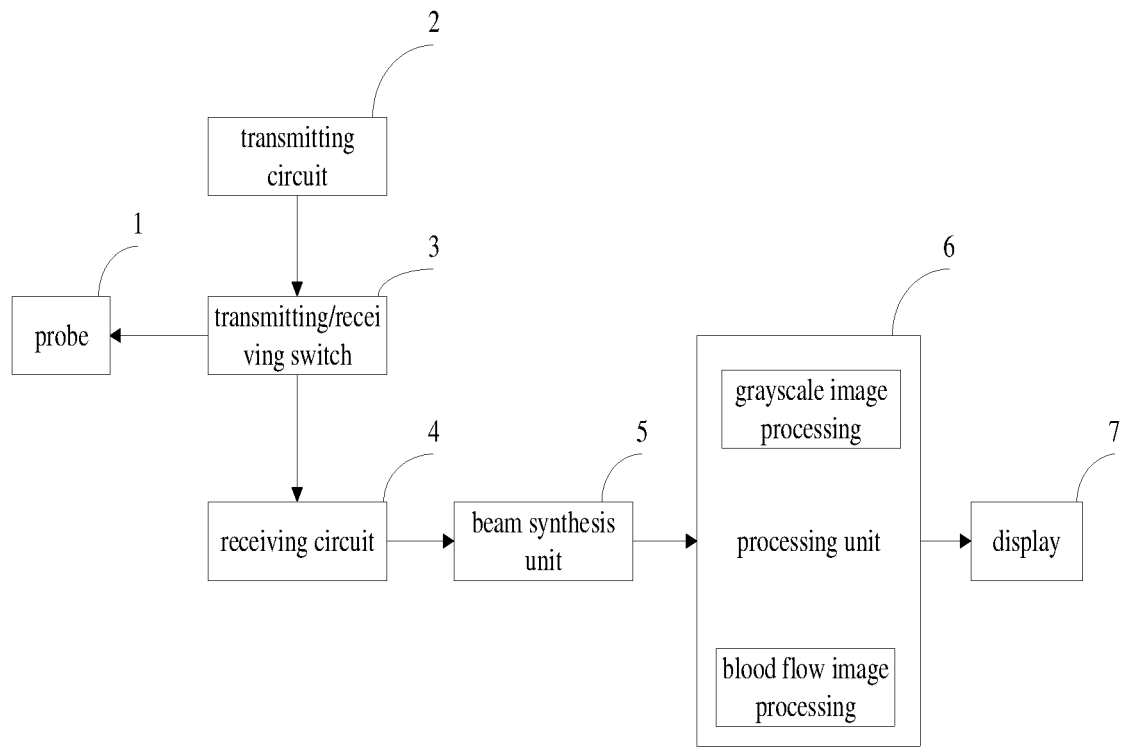
FIG. 3 is a schematically structural diagram of an ultrasound imaging system according to an embodiment of the present disclosure.

FIG. 3 is a schematically structural diagram of an ultrasound imaging system according to an embodiment of the present disclosure. As shown in FIG. 3, the ultrasound imaging system may include: a probe 1, a transmitting circuit 2, a transmitting/receiving switch 3, a receiving circuit 4, a beam synthesis/beamforming unit 5, a processor 6 and a display 7.

In the ultrasound imaging system, the transmitting circuit 2 may generate transmitting pulse sequences having certain amplitude and polarity as required, the pulse sequences may be transmitted to the probe 1 via the transmitting/receiving switch 3 and form a group of transmission time delays to control the probe 1. The probe 1, excited by the transmitting pulses, may transmit ultrasonic beams to a scan target for scanning, receive ultrasonic echoes reflected by a target region of the scan target after a certain time interval, and convert the ultrasonic echoes into electric signals. The receiving circuit 4 may receive the electric signals converted by the probe 1 to obtain ultrasonic echo signals and send the ultrasonic echo signals to the beam synthesis unit 5. The beam synthesis unit 5 may perform processing, such as focus delaying, weighting, and channel summing, etc., on the ultrasonic echo signals and then send the ultrasonic echo signals to the signal processor 6 where related signal processing procedures will be performed. The processor 6 may perform processing on the ultrasonic echo signals in different ways according to the imaging modes required by a user in order to obtain image data in different modes. Thereafter, the image data may undergo the processing, such as logarithmic compression, dynamic range adjustment, and digital scan conversion, etc., to form image data of different modes. The image data generated by the processor 6 may be sent to the display 7 to be displayed.

The ultrasound imaging system of the present disclosure can implement ultrasound blood flow imaging and gray scale imaging. The processor 6 can perform grayscale image processing on the synthesized ultrasonic echo signals to generate a grayscale ultrasonic image (hereinafter referred to as ultrasonic image), and can also perform wall filtering or spot tracking on the synthesized ultrasonic echo signals to obtain blood flow velocity vector information of a target point in the scan target. The display 7 can simultaneously display the ultrasonic image and the blood flow velocity vector information.

The probe 1 may generally include an array of a plurality of transducers. Each time the ultrasonic beams are transmitted, all or a part of the transducers of the probe 1 may be used. The used transducers may be excited by the transmitting pulses to transmit ultrasonic waves. The ultrasonic waves may be superimposed during the propagation such that resultant ultrasonic beams that are transmitted to the scan target can be generated. The direction of the resultant ultrasonic beams may be the "ultrasonic waves propagation direction" mentioned below. In the present disclosure, the angle between the ultrasonic waves propagation direction and the normal direction of the plane on which the transducers of the probe 1 are arranged is further referred to as the "steered angle of the ultrasonic beam".

Figure 4:
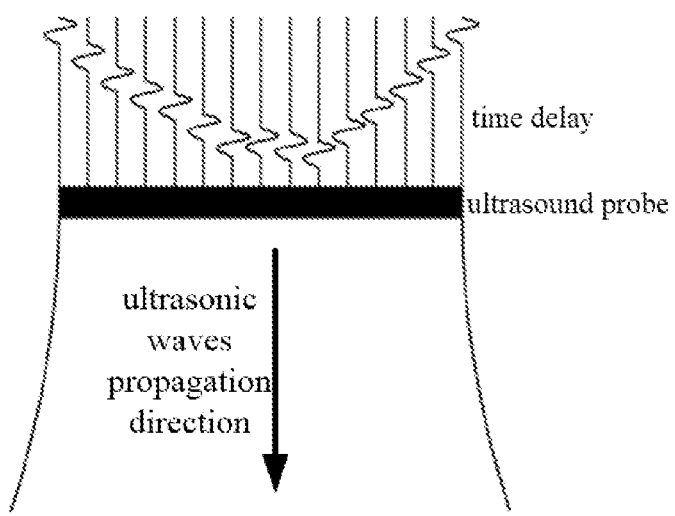
FIG. 4 is a schematic diagram of divergent ultrasound beams.

In the ultrasound imaging system of the present disclosure, divergent ultrasound beams are used to perform blood flow imaging. By controlling the time delays between the excitation times of the used transducers by the transmitting pulses, it may be possible that the ultrasonic waves transmitted by the used transducers diffuse during the propagation to form divergent waves which are substantially diffuse as a whole. In the present disclosure, such diffused ultrasonic beams may be referred to as the "divergent ultrasound beams". FIG. 4 is a schematically diagram of the divergent ultrasound beams in the ultrasonic waves propagation direction, in which the black arrow may represent the ultrasonic waves propagation direction of the divergent ultrasound beams. The divergent ultrasound beams will not be focused but diffused outward in the propagation direction after emitted from the plane on which the transducers of the probe 1 are arranged. The divergent ultrasound beams generally covers the entire imaging area of the probe 1. Therefore in the case of performing imaging using the divergent ultrasound beams, one frame of ultrasonic image may be obtained by one transmission.

Figure 6:
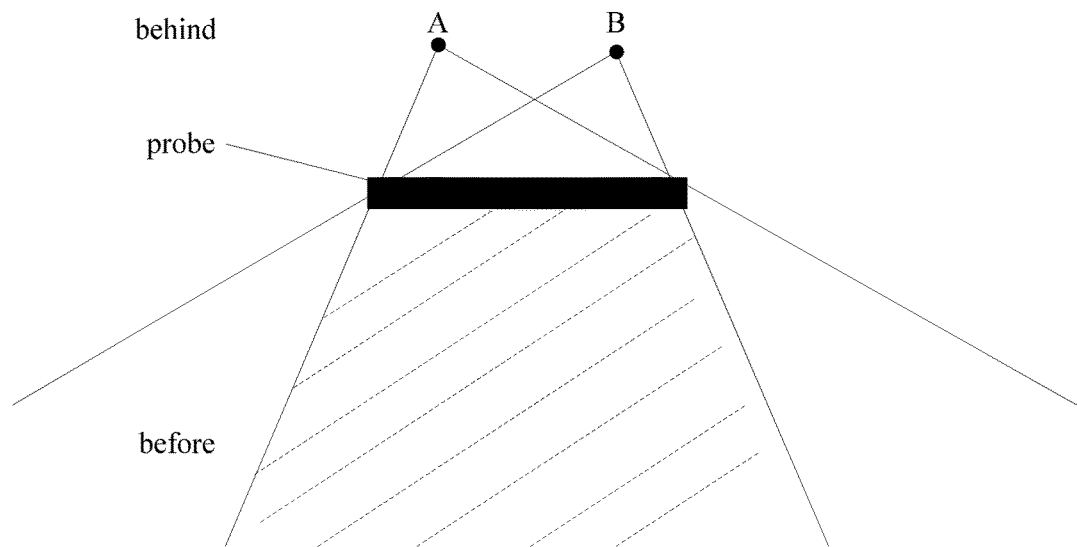
FIG. 6 is a schematic diagram of vector flow imaging using an ultrasound probe to transmit divergent ultrasound beams.

The processor 6 can perform a fitting calculation on the divergent ultrasound beams to be emitted by the probe 1, and thereby determine a virtual focus of the divergent ultrasound beams behind the plane on which the transducers of the probe 1 are arranged (as shown in FIG. 6). The virtual focus may refer to a focused position in the reverse propagation direction of the divergent ultrasound beams. Such position which is located behind the plane on which the transducers of the probe 1 are arranged may be referred to as a focus of the reverse propagation. In some embodiments, the divergent ultrasound beams can be focused at a position behind the probe 1, in this respect, the processor 6 can directly obtain the virtual focus. In some embodiments, the divergent ultrasound beams may be concentrated in intensity within only one region behind the probe 1; in this respect, the processor 6 can first determine a virtual focus area of the divergent ultrasound beams behind the probe, and then regard the center of the virtual focus area as the virtual focus. Such center may be regarded as the focus of the reverse propagation. The divergent ultrasound beams with different virtual focuses may correspondingly have different ultrasonic waves propagation directions, and the divergent ultrasound beams with different virtual focuses may have different scanning areas when scanning the scan target. The scanning area herein may refer to an area corresponding to the beams received by the probe for subsequent image processing. In the present disclosure, the scan target may be scanned with divergent ultrasound beams having different virtual focuses, and ultrasound blood flow imaging may be performed on the scan target in the overlapping scanning area of the divergent ultrasound beams. The ultrasound blood flow imaging performed with the divergent ultrasound beams will be described in detail below.

An ultrasound blood flow imaging method based on a divergent ultrasound beams may be provided in the present disclosure. The method may include: transmitting divergent ultrasound beams having different virtual focuses to a scan target at least twice, receiving echoes of divergent ultrasound beams with different virtual focuses to obtain multiple groups of divergent ultrasonic echo signals, calculating the velocity vector of a target point within a region to be scanned in the scan target based on each group of divergent ultrasonic echo signals, and then performing velocity synthesis on the velocity vectors which are obtained based on all groups of divergent ultrasonic echo signals to obtain the blood flow velocity vector information of the target point. The blood flow velocity vector information can be dynamically displayed in the form of a projection body. In order to better reflect the actual velocity of the target point, it is necessary to scan the corresponding scan target by divergent ultrasound beams having at least two different virtual focuses, for example, two, three or more virtual focuses. Each divergent ultrasound beams having individual virtual focus may be transmitted at least twice in a time-sharing manner so as to calculate the moving velocity (size and direction) of the target point under the corresponding divergent ultrasound beams.

An ultrasound blood flow imaging method provided in the present disclosure may include: transmitting at least twice first divergent ultrasound beams having a first virtual focus to a scan target and second divergent ultrasound beams having a second virtual focus to a scan target through a probe. The first scanning area of the first divergent ultrasound beams may cover the to-be-scanned region of the scan target, and the second scanning area of the second divergent ultrasound beams may cover the to-be-scanned region of the scan target. One frame of ultrasonic image can be obtained by one transmission of the first divergent ultrasound beams or the second divergent ultrasound beams, and both the first scanning area and the second scanning area can cover the to-be-scanned region of the scan target. The to-be-scanned region herein may be a complete anatomical structure (tissue or organ) of the scan target, or a local region of an anatomical structure that meets the needs of the user. The target point that the user wants to track and observe is located in the region to be scanned.

The position of the first virtual focus relative to the probe may be different from the position of the second virtual focus relative to the probe, and correspondingly the scanning range of the first scanning area and that of the second scanning area may be also different. In this respect, the first scanning area and the second scanning area may be overlapped at least partially, and the overlapped scanning area may cover the to-be-scanned region of the scan target, so that the blood flow imaging may be performed on the target point in the to-be-scanned region based on the first divergent ultrasound beams and the second divergent ultrasound beams.

When the probe transmits the first divergent ultrasound beams, the transmitting circuit may, with a first group of transmission time delays, excite the plurality of transducers of the probe to transmit ultrasonic waves to the scan target in a time-sharing manner to form the first divergent ultrasound beams. For the first group of transmission time delays, the transmission time of the ultrasonic waves emitted by the transducers closer to the first virtual focus is earlier than the transmission time of the ultrasonic waves emitted by the transducers far away from the first virtual focus, so that the ultrasonic waves successively emitted by the used transducers may be spatially composited to form the first divergent ultrasound beams in the first ultrasonic waves propagation direction. The first divergent ultrasound beams is reversely focused on the first virtual focus. When the probe transmits the second divergent ultrasound beams, the transmitting circuit may, with a second group of transmission time delays, excite the plurality of transducers of the probe to transmit ultrasonic waves to the scan target in a time-sharing manner to form the second divergent ultrasound beams. For the second group of transmission time delays, the transmission time of the ultrasonic waves emitted by the transducers closer to the second virtual focus is earlier than the transmission time of the ultrasonic waves of emitted by the transducers far away from the second virtual focus, so that the ultrasonic waves successively emitted by the used transducers may be spatially composited to form the second divergent ultrasound beams in the second ultrasonic waves propagation direction. The second divergent ultrasound beams is reversely focused on the second virtual focus.

Since the first virtual focus and the second virtual focus may be positioned differently in space relative to the probe, the transmission time delays of the first group and the transmission time delays of the second group may be also different. For example, in a first case that multiple transducers used in the transmission of the first divergent ultrasound beams and the second divergent ultrasound beams may be the same, the transmitting sequences of a same transducer in the first and second groups of the transmission time delays may be different, thereby forming different transmission sequences of the transducers in the first and second groups of transmission time delays. For example, in a second case that multiple transducers used in the transmission of the first divergent ultrasound beams and the second divergent ultrasound beams may be partly or all different, since the used transducers are different, the transmission sequence of each transducer with reference to the first and second groups of the transmission time delays respectively may also be different. In the second case, even if the transmission time of each transducer in the first group of transmission time delays and that in the second group of transmission time delays are the same, but due to the difference of the used transducers, the position of the transducers on the plane on which the ultrasound probe is arranged will be changed; and in this respect, the first group of transmission time delays and the second group of transmission time delays may be regarded as different transmission time delays.

Subsequently, the echoes of the first divergent ultrasound beams may be received to obtain a group of first divergent ultrasonic echo signals which may include at least two first divergent ultrasonic echo signals. The processor may, based on the group of the first divergent ultrasonic echo signals, calculate a first velocity vector in a first direction of the target point within the to-be-scanned region of the scan target. Similarly, the echoes of the second divergent ultrasound beams may be received to obtain a group of second divergent ultrasonic echo signals which may include at least two second divergent ultrasonic echo signals. The processor may, based on the group of the second divergent ultrasonic echo signals, calculate a second velocity vector in a second direction of the target point within the to-be-scanned region of the scan target. The processor may further generate the blood flow velocity vector information of the target point in the to-be-scanned region based on the first velocity vector and the second velocity vector. For example, velocity synthesis may be performed on the first velocity vector and the second velocity vector to obtain a vector velocity that can reflect actual movement of the target point as much as possible.

The above-mentioned blood flow velocity vector information can be dynamically displayed in the form of a moving projection body. The position of the projection body may be dynamically updated between each frame of divergent ultrasonic echo signals and thereby form a trajectory of the projection body, which can reflect the trajectory of the movement of the target point in the to-be-scanned region. The projection body can be color coded, and the color or chroma of the color code may be related to the velocity of the target point. The projection body may have a certain length which may be related to the velocity of the target point. The front end of the projection body may have an arrow for indicating the direction of movement of the projection body, and the direction indicated by the arrow may correspond to the velocity direction of the target point, that is, correspond to the direction of the fluid at the target point.

The above-mentioned blood flow velocity vector information can also be displayed in a static manner. For example, a velocity indicator may be marked at the position of the target point on the image of the current frame. The blood flow velocity vector information of the target point may be statically displayed by the dimension and orientation of the velocity indicator. For example, the orientation of the velocity indicator may indicate the movement direction of the blood flow at the target point, and the size of the projection body may indicate the velocity of the blood flow at the target point.

Although the first divergent ultrasound beams and the second divergent ultrasound beams are used to describe, the "first" and "second" herein are not used to limit the divergent ultrasound beams to the divergent ultrasound beams with two different virtual focuses; instead, the divergent ultrasound beams with more than one virtual focus to perform ultrasound blood flow imaging in the present disclosure.

Compared with traditional ultrasound blood flow imaging, ultrasound blood flow imaging disclosed in the present disclosure can expand the scanning area by using the divergent ultrasound beams, and the overlapped region of the divergent ultrasound beams can be significantly increased, especially it can basically cover the entire heart when applied to cardiac ultrasound imaging. Hereinafter, the present disclosure will be further described in detail through specific embodiments accompanying with the drawings.

Figure 5:
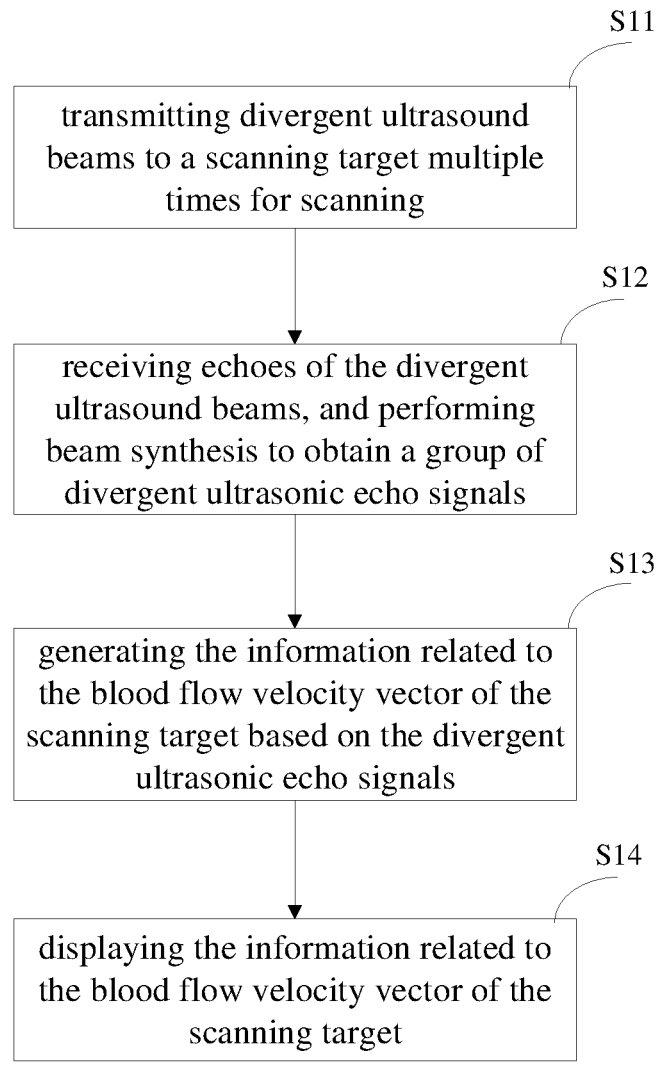
FIG. 5 is a schematic flowchart of an ultrasound blood flow imaging method according to an embodiment of the present disclosure.

FIG. 5 is a schematic flowchart of an ultrasound blood flow imaging method according to an embodiment of the present disclosure. The ultrasound blood flow imaging method may use divergent ultrasound beams to scan a scan target, and specifically includes steps S11-S14.

In step S11, the divergent ultrasound beams may be transmitted to the scan target, and the scan target may be scanned by the divergent ultrasound beams. The divergent ultrasound beams may be configured to obtain divergent ultrasonic echo signals, which are used to perform ultrasound blood flow imaging. According to the needs of vector flow imaging, ultrasonic beams are required to be transmitted multiple times. In the ultrasound blood flow imaging method of the present disclosure, the scan target may be scanned by the divergent ultrasound beams in different ultrasonic waves propagation directions (i.e. the beams having different virtual focuses), the divergent ultrasound beams in each ultrasonic waves propagation direction (i.e. corresponding to different virtual focuses) may be transmitted at least twice to determine velocity vectors of the scan target during scanning respectively, and the velocity vectors may be synthesized to obtain the blood flow velocity vector information of the scan target. In step S11, the divergent ultrasound beams may be transmitted in different ultrasonic waves propagation directions to the scan target, wherein the divergent ultrasound beams may have different virtual focuses and different sound field coverage. The ultrasound blood flow imaging may be performed on the scan target covered by the sound field overlap region of these divergent ultrasound beams.

Figure 1:
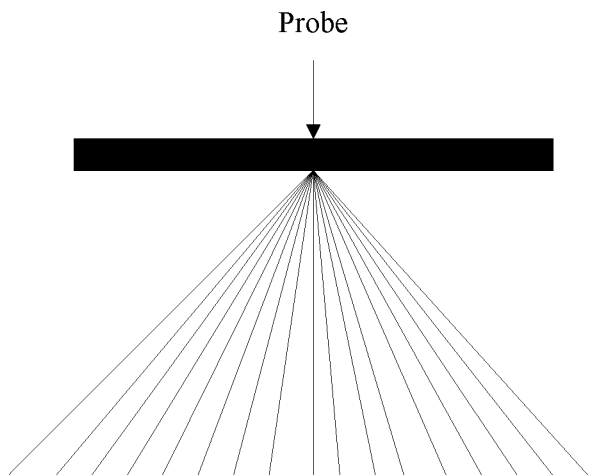
FIG. 1 is a schematic diagram of line-by-line ultrasound scanning using an ultrasound probe.
Figure 2:
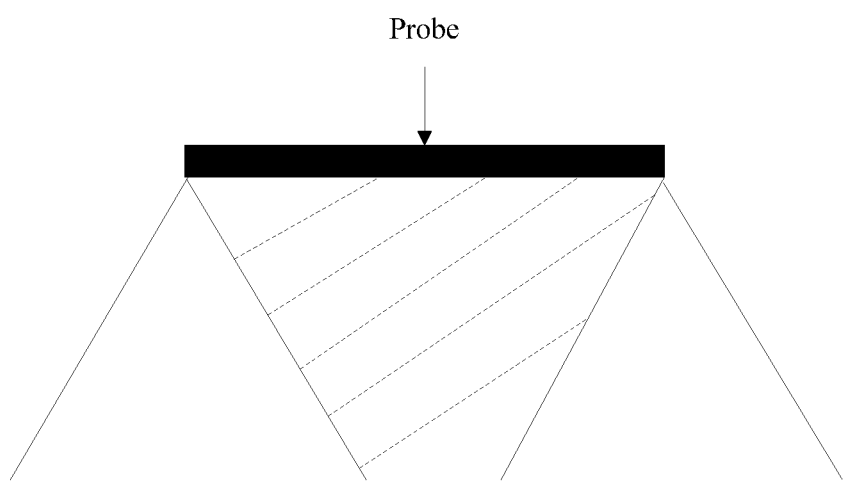
FIG. 2 is a schematic diagram of vector flow imaging using an ultrasound probe to transmit plane waves.

The use of two divergent ultrasound beams is taken as an example, as shown in FIG. 6, the ultrasound probe may transmit first divergent ultrasound beams having a first virtual focus A and second divergent ultrasound beams having a second virtual focus B in two different ultrasonic waves propagation directions. The first and second divergent ultrasound beams may respectively form two transmitted sound fields, which may be at least partially overlapped. The overlapped region (indicated by the dashed line in the figure) is the scanning area where ultrasound blood flow imaging is performed on the scan target. This overlapped scanning area, referred to as a target scanning area in the present disclosure, can cover the to-be-scanned region of the scan target. As can be seen in the figure, when performing ultrasound blood flow imaging, compared to the use of traditional plane waves (see FIG. 2), the overlapped scanning area of the first and second divergent ultrasound beams (i.e. target scanning area) may be a substantially trapezoidal scanning area. The scanning range of the scanning area may be significantly increased, and especially when it is applied to cardiac ultrasound scanning, it can basically cover the heart of the scan target. With reference to FIG. 6, the substantially trapezoidal scanning area herein may mean that the bottom (i.e. the position away from the plane on which the transducers are arranged) size of the scanning area is larger than the top (i.e. the position close to the plane on which the transducers are arranged) size of the scanning area; in this respect the scanning range may be increased in the propagation direction of the divergent ultrasound beams, thereby providing a wider target scanning area, which is beneficial to completely cover the to-be-scanned region of the scan target. In some embodiments, the bottom of the substantially trapezoidal scanning area may be arc-shaped.

As described above, by controlling the time delays between the excitation times of the used transducers by the transmitting pulses, divergent ultrasound beams that diffuse during the propagation can be obtained. The transducers involved in the transmission of ultrasonic beams may generally arranged in an array, and by controlling the transducers in the array to transmit ultrasonic waves with different delays, divergent ultrasound beams can be obtained. For example, according to the distance between each transducer and the virtual focus, the transducer with a short distance may be controlled to transmit ultrasonic waves before the transducer with a long distance, thereby obtaining the divergent ultrasound beams.

Figure 7A:
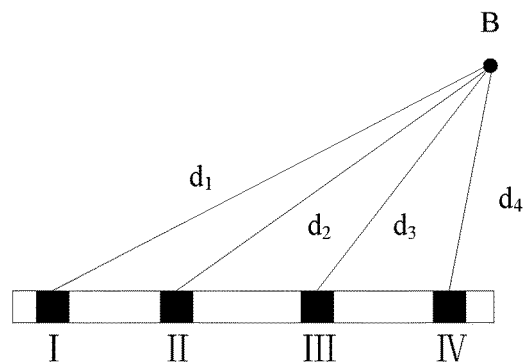
FIG. 7a and FIG. 7b are schematic transmission of the divergent ultrasound beams transmitted by the ultrasonic probe with four transducers.
Figure 7B:
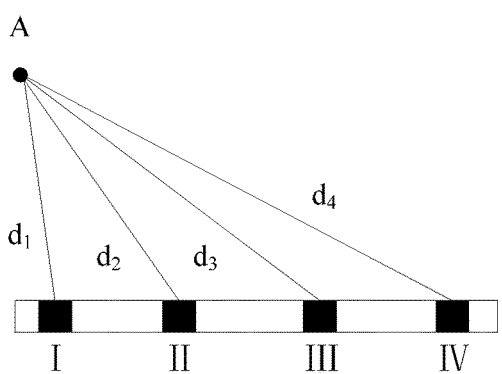

Specifically, as shown in FIG. 7a, taking an ultrasound probe having four transducers as an example to illustrate how to adjust the time delays of the used transducers in the probe so as to obtain the divergent ultrasound beams. First, a virtual focus (virtual focus B as shown in the figure) behind the probe may be determined, and the relative delay of each transducer may be calculated based on the distance from the virtual focus to each corresponding transducer. The dark blocks in FIG. 7 may represent transducers I, II, III, IV respectively, and $d_1$, $d_2$, $d_3$, $d_4$ may represent the distance from the virtual focus B to transducers I, II, III, IV respectively. The time from virtual focus B to each transducer is $t_i = d_i/c$, where i may represent the transducer number, and c may represent sound velocity. According to $t_i$, the delay of each transducer may be $Delay_i = t_i - \min(t_i)$, where $Delay_i$ may represent the transmission time delay of the i-th transducer. The four transducers may transmit ultrasonic waves according to the transmission time delays mentioned above, and the divergent ultrasound beams having the second virtual focus B as shown in the figure may be compositely formed during the propagation.

With the arrangement of the virtual focus and the transducers shown in FIG. 7a, the sequence in which transducers I, II, III, IV transmit ultrasonic waves may be: transducer IV, transducer III, transducer II and transducer I. In the same way, with the arrangement of the virtual focus and the transducers shown in FIG. 7b, the sequence in which transducers I, II, III, IV transmit ultrasonic waves may be: transducer I, transducer II, transducer III and transducer IV. It can be seen from FIG. 7a and FIG. 7b, by controlling the transmission time delays of the transducers I, II, III, IV, divergent ultrasound beams in different ultrasonic waves propagation directions can be obtained.

It is not limited to using divergent ultrasound beams with two different virtual focuses in ultrasound blood flow imaging. A user can use divergent ultrasound beams with three or more different virtual focuses as required. When transmitting divergent ultrasound beams to the scan target to conduct scanning, divergent ultrasound beams with different virtual focuses (i.e. different ultrasonic waves propagation directions) can be transmitted alternately for scanning.

Figure 8A:
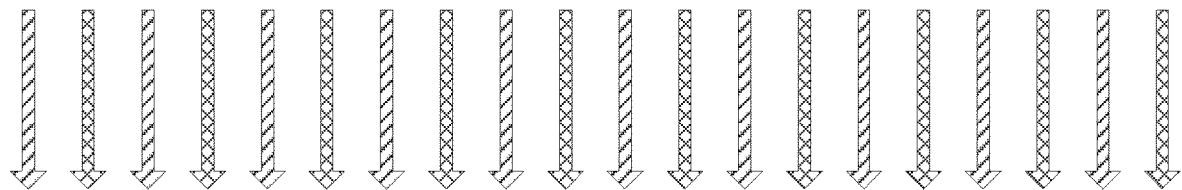
FIG. 8a is a schematic diagram of transmitting pulse sequences in which divergent ultrasound beams having two different divergent ultrasound beams are alternately transmitted by the ultrasound probe.
Figure 8B:
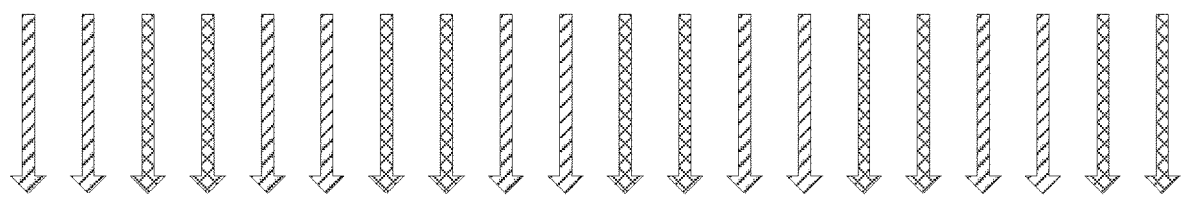
FIG. 8b is a schematic diagram of another transmitting pulse sequences in which divergent ultrasound beams having two different divergent ultrasound beams are alternately transmitted by the ultrasound probe.
Figure 8C:
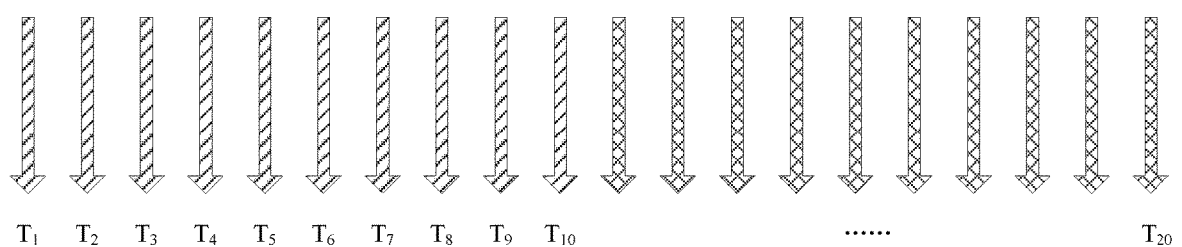
FIG. 8c is a schematic diagram of still another transmitting pulse sequences in which divergent ultrasound beams having two different divergent ultrasound beams are alternately transmitted by the ultrasound probe.

FIGS. 8a-8c schematically show diagrams of the transmitting pulse sequences of divergent ultrasound beams with two different virtual focuses being transmitted alternately, where different patterns represent the divergent ultrasound beams with different virtual focuses. In FIG. 8a, the first divergent ultrasound beams and the second divergent ultrasound beams may be alternately scanned frame by frame. In FIG. 8b, the first divergent ultrasound beams and the second divergent ultrasound beams may be scanned alternately every two frames; in this respect, after the divergent ultrasound beams with different virtual focuses may be used for scanning every two frames, the blood flow velocity vector information may calculated subsequently. In FIG. 8c, the first divergent ultrasound beams can be used for scanning first to obtain all the echo signals used for calculating blood flow velocity vector information, and then the second divergent ultrasound beams can be alternately transmitted for scanning. $T_1$-$T_{10}$ in FIG. 8c may be regarded as forming a calculation package for calculating the blood flow velocity vector information, which is, in FIG. 8c, the first divergent ultrasound beams and the second divergent ultrasound beams may be alternately scanned packet by packet. The calculation package composed of $T_1$-$T_{10}$ is only used for illustration, and does not limit the number of transmission of the divergent ultrasound beams required by the calculation package. For example, the first divergent ultrasound beams for every two frames and the second divergent ultrasound beams for every two frames shown in FIG. 8b can also form a calculation package for calculating the blood flow velocity vector information.

Figure 8D:
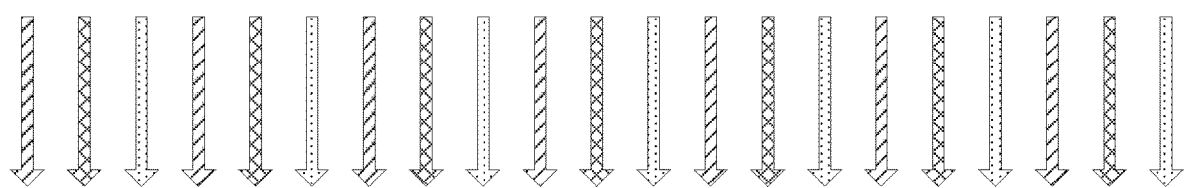
FIG. 8d is a schematic diagram of another transmitting pulse sequences in which divergent ultrasound beams having three different divergent ultrasound beams are alternately transmitted by the ultrasound probe.

When using the divergent ultrasound beams with three different virtual focuses for scanning, any one manner shown in FIGS. 8a-8c may be used for alternate scanning. FIG. 8d shows a transmission mode in which the divergent ultrasound beams with three different virtual focuses may be alternately scanned frame by frame.

With the divergent ultrasound beams, a wider scanning area can also be obtained due to the divergent characteristics, even it is applied to a UCG examination, thus well covering the heart of the scan target. When a phased array probe is used for vector flow imaging, by means of the ultrasound blood flow imaging method based on divergent ultrasound beams, and by controlling the phased array probe to transmit the divergent ultrasound beams with different virtual focuses, the heart of the scan target can be covered by the target scanning area formed by the overlapped scanning area of the beams, thereby meeting the imaging needs of a UCG examination.

In step S12, the echo of the divergent ultrasound beams may be received, and a group of divergent ultrasonic echo signals is obtained through beam synthesis. For example, after transmitting the first divergent ultrasound beams and the second divergent ultrasound beams multiple times in step S11, the echoes of the first divergent ultrasound beams and the second divergent ultrasound beams may be received respectively, thereby obtaining a group of first divergent ultrasonic echo signals and a group of second divergent ultrasonic echo signals.

Figure 9:
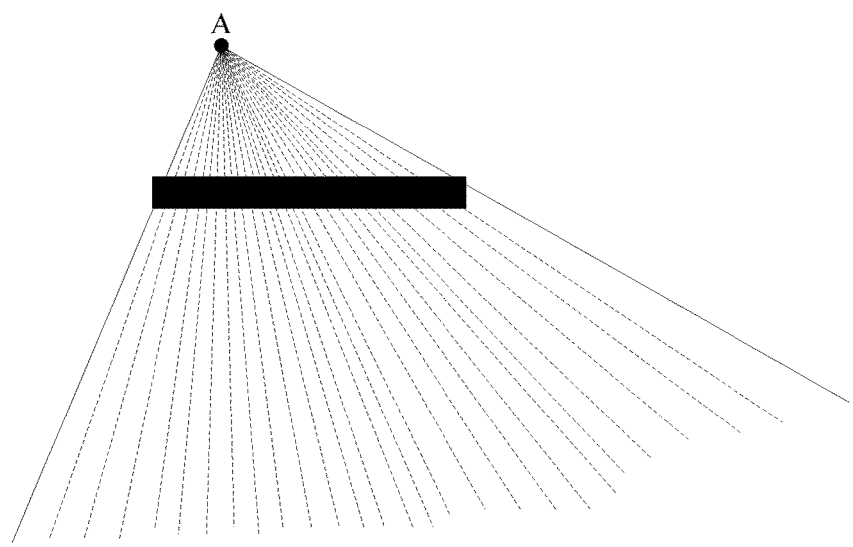
FIG. 9 schematically shows divergent lines of the divergent ultrasound beams.

As shown in FIG. 9, the transmitted sound field of the first divergent ultrasound beams may have divergent lines emitted outward with virtual focus A. The divergent lines may correspond to a position where the intensity of ultrasonic waves in the transmitted sound field is concentrated relative to the surrounding space. In an implementation, step S12 may perform beam synthesis based on divergent lines, and the final beamformed image may be composed of the values of the divergent lines. In another embodiment, step S12 may perform beam synthesis based on pixels in the scanning area of the divergent ultrasound beams.

In step S13, the blood flow velocity vector information of the scan target may be obtained according to the divergent ultrasonic echo signals. Specifically, after obtaining a group of divergent ultrasonic echo signals with a certain virtual focus, the target point to be calculated by vector flow may be determined, and then the direction and magnitude of the velocity of the target point may be calculated to generate the velocity component of the target point under the scanning by the group of the divergent ultrasound beams. The moving distance of the target point within a certain time interval may be calculated, and the phase difference of the target point within a certain time interval may also be calculated to obtain the velocity of the target point. The velocity component of the target point under the scanning by a group of the divergent ultrasound beams with another virtual focus may also be calculated by the same method. All the velocity components obtained under different virtual focuses may be synthesized to obtain the vector velocity, that is, the blood flow velocity vector information of the target point.

Figure 10:
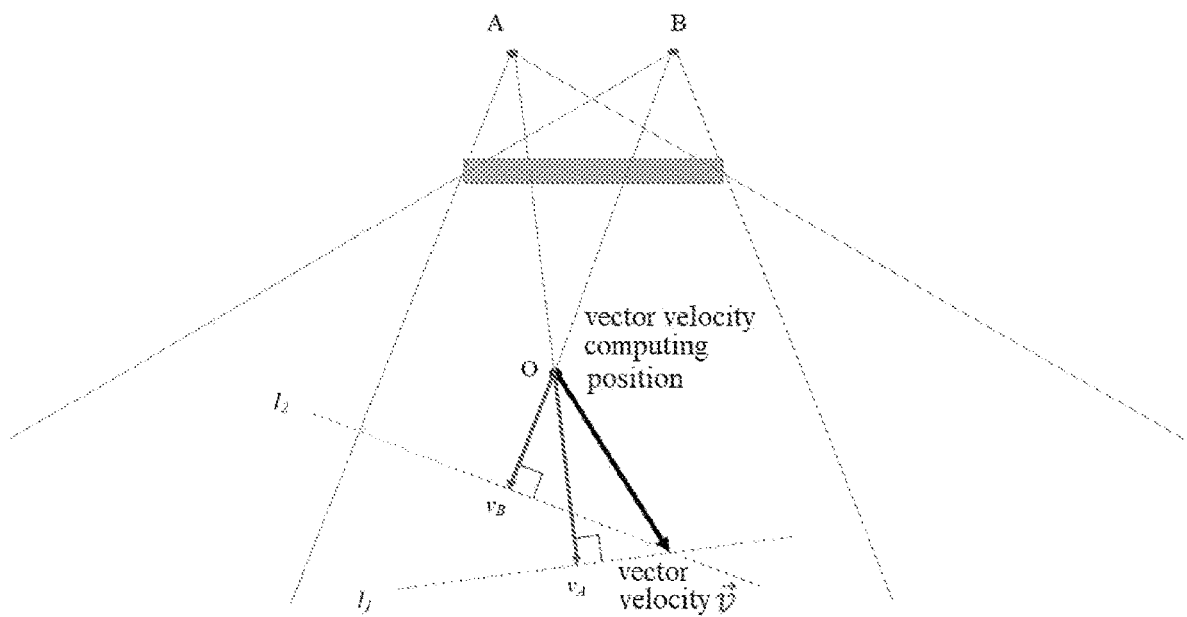
FIG. 10 is a schematic diagram of calculating the vector velocity of a certain target point in FIG. 5.

FIG. 10 is a schematic diagram of calculating the vector velocity of a certain target point in FIG. 5. After scanning with the first diffuse ultrasonic beams of the virtual focus A, a velocity component $v_A$ of the target point in a first direction may be calculated. The first direction may be coincided with the direction of a connecting line that connects the target point to the virtual focus A. After scanning with the second diffuse ultrasonic beams of the virtual focus B, a velocity component $v_B$ of the target point in a second direction may be calculated. The second direction may be coincided with the direction of a connecting line that connects the target point to the virtual focus B. The illustrated vector velocity $\vec{v}$ may be acquired by performing angle synthesis on $v_A$ and $v_B$. As shown in the figure, a first reference line $l_1$ perpendicular to the first direction may be determined based on the velocity component $v_A$, the second reference line $l_2$ perpendicular to the second direction may be determined based on the velocity component $v_B$, and the direction of the vector velocity $\vec{v}$ of the target point may be the direction of a connecting line that connecting the target point to the intersection O of the first reference line $l_1$ and the second reference line $l_2$.

FIG. 10 specifically illustrates how to acquire the velocity vector of the target point when scanning by the divergent ultrasound beams with two different virtual focuses. In order to obtain the velocity vector of a certain target point, the divergent ultrasound beams with two or more different virtual focuses may be used for scanning to obtain velocity components in two or more different directions, and the velocity components may be performed with velocity vector synthesis. The divergent ultrasound beams with different virtual focuses may correspond to different transmitting angles. The more scanning the same target point from more angles, the higher the signal-to-noise ratio, and the more accurate the final calculated velocity vector.

In step S13, when calculating the blood flow velocity vector information, the synthesized divergent ultrasonic echo signals may be performed wall filtering to obtain blood flow signals, and the velocity components may be calculated by using the blood flow signals under each virtual focus respectively. The velocity component may be calculated by a traditional autocorrelation method, the formula thereof may be as follows $$v_k = -\frac{cf_{PRF}}{4\pi f_0}\arctan\left(\frac{\mathcal{J}\{R(1)\}}{\mathfrak{R}\{R(1)\}}\right)$$

$$R(1) = \frac{1}{N-1}\sum_{m=0}^{N-2} x(m)x(m+1) + y(m)y(m+1) + j[y(m+1)x(m) - x(m+1)y(m)]$$

where $v_k$ may represent the calculated velocity component under the k-th focus, $f_0$ may represent the center frequency of the probe transmitting signals, $f_{PRF}$ may represent the transmission PRF (Pulse Repetition Frequency) of the same focus, N may represent the number of the transmitting, x(m) may represent the real part of the m-th transmitted, received and processed signal, y(m) may represent the imaginary part of the m-th transmitted, received and processed signal, $\mathcal{J}$ is taking-imaginary part operator, $\mathfrak{R}$ is taking-real part operator, and j is imaginary unit.

In addition to the autocorrelation method for calculating the velocity component, the existing spot tracking method in the field can also be used for calculation.

In step S14, the blood flow velocity vector information of the scan target may be displayed. What is displayed here is the blood flow velocity vector information of the target point within the selected scan target. The calculated blood flow velocity vector information may be displayed as a projection body which may be moved in real time as the position of the position of the target point changes. The projection body may be an arrow starting from the location of the target point, and the direction of the arrow may indicate the direction of blood flow at the target point. The projection body may be a line segment with an arrow end starting from the location of the target point. Color coding may be performed on the projection body, wherein the color and chroma of the color coding correspond to the velocity of the target point, and the length of the projection body may also correspond to the velocity of the target point. Based on such display manner, the faster the target point moves within a certain time interval, the longer the projection body and the darker the color. According to the length and color of the projection body, a user can intuitively appreciate the blood flow of the scan target in each time period. For example, when applied to a UCG examination, with the displayed blood flow velocity vector information, the user can easily see the velocity of blood flow in the heart and know the pumping ability of the heart.

Figure 11:
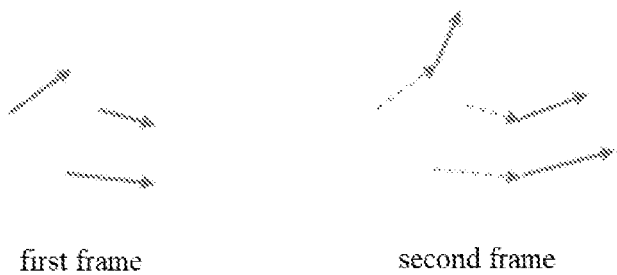
FIG. 11 is a schematic diagram showing blood flow velocity vector information in an embodiment of the present disclosure.

FIG. 11 is a schematic diagram showing the blood flow velocity vector information in an embodiment of the present disclosure. As shown in the figure, the blood flow velocity vector information can be displayed in the form of a projection body, and with the movement of a corresponding target point, it is dynamically displayed in motion between each frame of images, and the motion trajectory of the projection body may be formed. The trajectory of the projection body can intuitively and truly reflect the actual movement direction of the fluid at the target point; in contrast, traditional blood flow imaging (C mode) can only indicate the relative movement trend (moving toward or away from the probe) of the fluid according to the ultrasonic waves propagation direction. The length or size of the projection body can intuitively and truly reflect the actual velocity of the fluid at the target point; in contrast, traditional Doppler imaging (D mode) can only calculate the velocity along the ultrasonic waves propagation direction or perform direction correction according to the velocity in the ultrasonic waves propagation direction to estimate the velocity of the target point.

By means of the ultrasound blood flow imaging method mentioned above, a wide overlapping scanning area may be formed by using the divergent ultrasound beams, thus achieving approximately trapezoidal high-frame-rate cardiac vector flow imaging. In this respect, when the phased array probe is used for a UCG examination, the coverage of the scanning area will no longer be affected by the width of the probe, and vector flow imaging can be quickly realized.

When applying the above ultrasound blood flow imaging method to ultrasound blood flow imaging for the heart, the following steps may be included. In this example, the heart may be a region to be scanned for the scan target.

The probe may be excited by the transmitting circuit to alternately transmit the divergent ultrasound beams with multiple different virtual focuses (or they may be referred to as different ultrasonic waves propagation directions) to the heart of the scan target. The scanning area, defined in a composite manner by the divergent ultrasound beams during the propagation, may be the target scanning area which can cover the heart of the scan target. As mentioned above, the divergent ultrasound beams with two, three or more virtual focuses may be used for alternate scanning. Each divergent ultrasound beams of each virtual focus may be used for scanning at least twice for subsequent velocity component calculations. The specific alternate transmission mode can be described with reference to the foregoing.

The echoes of divergent ultrasound beams with different virtual focuses may be received and converted by the probe into first electric signals that may be transmitted to the receiving circuit and synthesized by the beam synthesis unit to obtain a group of divergent ultrasonic echo signals corresponding to different virtual focuses. The beam synthesis herein may be implemented based on the divergent line of the divergent ultrasound beams, or based on the pixel points in the target scanning area.

Based on each group of divergent ultrasonic echo signals of different virtual focuses, the processor may first calculate the direction and magnitude of the velocity of the target point in the heart of the scan target to obtain the velocity components corresponding to different virtual focuses, and perform angle synthesis on each velocity component to generate the blood flow velocity vector information of the target point in the heart. The specific calculation may be similar to the description above.

Finally, the blood flow velocity vector information of the target point in the heart may be dynamically displayed on the display, for example, a color-coded projection body can be used for display.

In the ultrasound blood flow imaging method, when displaying the blood flow velocity vector information, it is usually displayed in synchronization with the grayscale ultrasonic image of the scan target. In the ultrasound imaging system of one embodiment according to the present disclosure, gray-scale image processing may be performed on the divergent ultrasonic echo signals to obtain an ultrasonic image. That is, after the synthesized divergent ultrasonic echo signals are obtained, on the one hand wall filtering or spot tracking may be performed on the divergent ultrasonic echo signals to obtain the blood flow velocity vector information of each target point, and on the other hand an envelope detection algorithm may be carried out on the divergent ultrasonic echo signals to obtain the grayscale ultrasonic image of the scan target. In combination with the method shown in FIG. 5, step S13 may further include performing grayscale image processing according to divergent ultrasonic echo signals to obtain a two-dimensional grayscale ultrasonic image of the scan target. For example, when it is applied to a UCG examination, the ultrasonic image of the heart can be obtained based on divergent ultrasonic echo signals.

Figure 12:
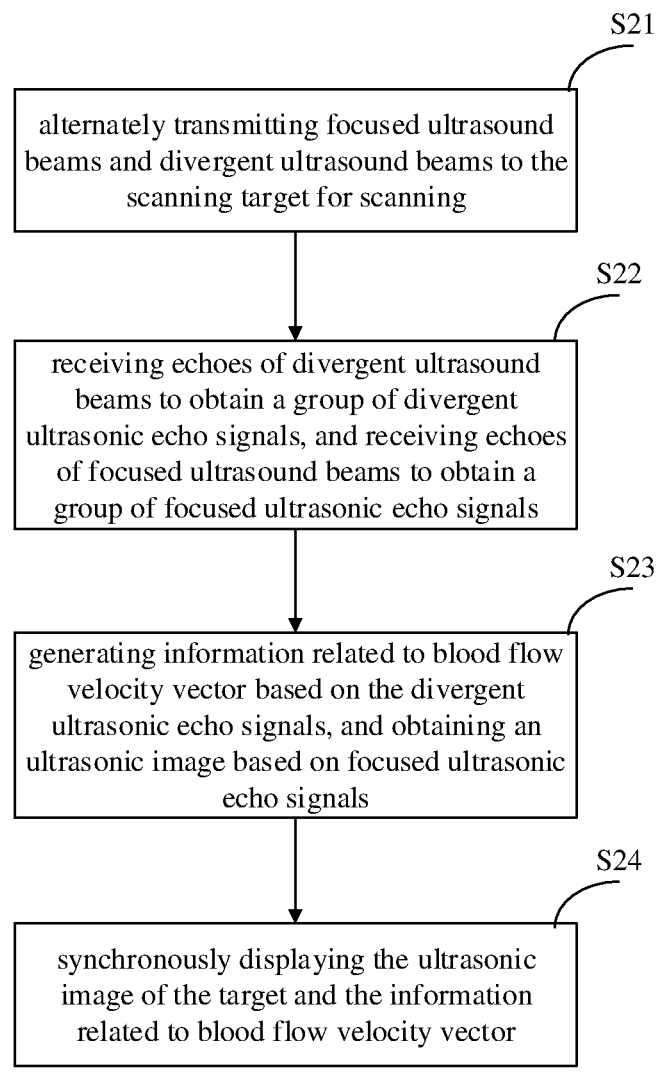
FIG. 12 is a schematic flowchart of an ultrasound blood flow imaging method according to another embodiment of the present disclosure.

In another embodiment, the ultrasound imaging system of the present disclosure may adopt transmission of divergent ultrasound beams and focused ultrasound beams for imaging, wherein the echo signals of the divergent ultrasound beams may be used for blood flow imaging, and the echo signals of the focused ultrasonic beams may be used for grayscale-image imaging. FIG. 12 is a schematic flowchart of an ultrasound blood flow imaging method according to another embodiment of the present disclosure. In the ultrasound blood flow imaging method, the divergent ultrasound beams may be used for vector flow imaging, and the focused ultrasound beams may be used for gray scale imaging. Specifically, the method may include the following steps S21-S24.

In step S21, focused ultrasound beams and divergent ultrasound beams may be alternately transmitted to the scan target for scanning. FIGS. 13a-13d schematically show transmitting pulse sequences that transmit focused ultrasound beams and divergent ultrasound beams alternately.

Figure 13A:
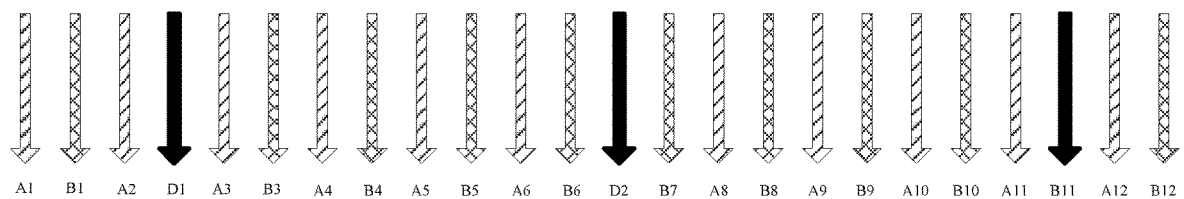
FIG. 13a is a schematic diagram of transmitting pulse sequences in which divergent ultrasound beams and focused ultrasound beams are alternately transmitted according to the embodiment shown in FIG. 9.
Figure 13B:
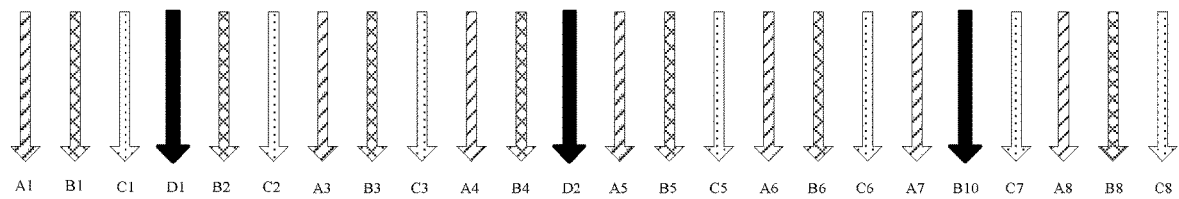
FIG. 13b is a schematic diagram of another transmitting pulse sequences in which divergent ultrasound beams and focused ultrasound beams are alternately transmitted according to the embodiment shown in FIG. 9.

Referring to FIG. 13a and FIG. 13b, they are corresponded to the divergent ultrasound beams of two different virtual focuses and the divergent ultrasound beams of three different virtual focuses respectively; and in this respect, the focused ultrasound beams inserted into the divergent ultrasound beams may replace the divergent ultrasound beams that was originally transmitted at the time of the insertion. The black solid arrow in the picture may represent focused ultrasonic waves.

As shown in FIG. 13a, Ai may represent the divergent ultrasound beams with the first virtual focus A transmitted to the scan target for an i-th time, Bi may represent the divergent ultrasound beams with the second virtual focus B transmitted to the scan target for an i-th time, and Di may represent the focused ultrasound beams transmitted to the scan target for an i-th time; in this case, the transmitting pulse sequences shown in FIG. 13a may be A1, B1, A2, D1, A3, B3, A4, B4, A5, B5, A6, B6, D2, B7, A8, B8, A9, B9, A10, B10, A11, D3, A12, B12. Among them, the focused ultrasound beams transmitted to the scan target for a first time may replace the divergent ultrasound beams of the second virtual focus B that were originally transmitted to the scan target for a second time at the time of insertion; and the focused ultrasound beams transmitted subsequently for the second, third, or i-th time can be done in a similar manner to replace the divergent ultrasound beam(s) at the time of insertion.

As shown in FIG. 13b, Ai may represent the divergent ultrasound beams with the first virtual focus A transmitted to the scan target for the i-th time, Bi may represent the divergent ultrasound beams with the second virtual focus B transmitted to the scan target for the i-th time, Ci may represent the divergent ultrasound beams with the third virtual focus C transmitted to the scan target for the i-th time, and Di may represent the focused ultrasound beams transmitted to the scan target for the i-th time; in this case, the transmitting pulse sequences shown in FIG. 13b may be A1, B1, C1, D1, B2, C2, A3, B3, C3, A4, B4, D2, A5, B5, C5, A6, B6, C6, A7, D3, C7, A8, B8, C8. Among them, the focused ultrasound beams transmitted to the scan target for a first time may replace the divergent ultrasound beams of the second virtual focus A that were originally transmitted to the scan target for a second time at the time of insertion; and the focused ultrasound beams transmitted subsequently for the second, third, or i-th time can be done in a similar manner to replace the divergent ultrasound beam(s) at the time of insertion.

In the transmission scheme of FIGS. 13a-13b, since the focused ultrasound beams replace the divergent ultrasound beams in the transmitting pulse sequences, and part of the information related to the echoes of the divergent ultrasound beams may be lost during scanning the scan target with divergent waves. In order to ensure the continuity of the divergent ultrasonic echo signals, interpolation is used to supplement the divergent ultrasonic echo signals that are lost due to the insertion of the focused wave(s). When performing interpolation calculation, the echo signals of the divergent ultrasound beams with the same virtual focus may be used for interpolation. With reference to FIG. 13a, for the lost divergent ultrasonic echo signals of B2, interpolation calculation may be performed with the divergent ultrasonic echo signals of B1 and B3. With reference to FIG. 13b, for the lost divergent ultrasonic echo signals of A2, interpolation calculation may be performed with the divergent ultrasonic echo signals of A1 and A3. Interpolation calculation may be performed on the rest lost divergent ultrasonic echo signals, which will not be repeated herein.

Three groups of divergent ultrasonic echo signals corresponding to different virtual focuses may be obtained respectively after transmitted for the Ai, Bi, and Ci times and may be used for ultrasound blood flow imaging. That is, the velocity component of the target point of the scan target under each virtual focus may be calculated separately, and then the blood flow velocity vector information of the target point may be synthesized. In this respect, one frame of image may be obtained every Ai-th, every Bi-th and every Ci-th transmission. The focused ultrasonic echo signals may be obtained by scanning with the above focused ultrasound beams to be used for grayscale ultrasonic imaging. Scanning with focused ultrasound beams may need to synthesize the results of multiple transmission, that is, synthesizing the focused ultrasonic echo signals obtained by D1, D2, . . . , Di times and obtaining a frame of grayscale ultrasonic image through signal processing and image processing.

Figure 13C:
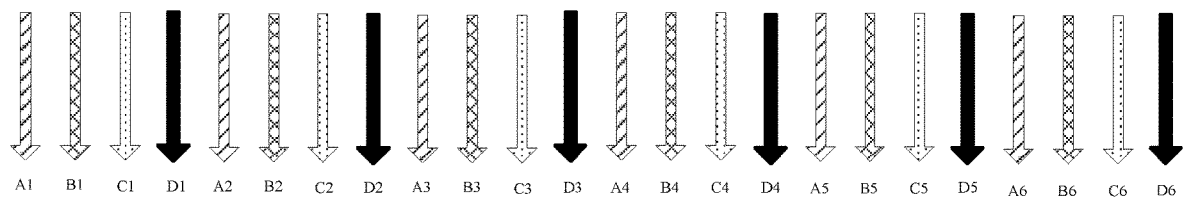
FIG. 13c is a schematic diagram of still another transmitting pulse sequences in which divergent ultrasound beams and focused ultrasound beams are alternately transmitted according to the embodiment shown in FIG. 9.

In order to ensure the continuity of the divergent ultrasound beams, in this present disclosure, transmitting pulse sequences as shown in FIG. 13c may be used to alternately transmit the divergent ultrasound beams and the focused ultrasound beams to the scan target. In FIG. 13c, the transmission may be implemented by alternately transmitting the divergent ultrasound beams transmitted continuously for multiple times and the focused ultrasound beams transmitted for one time in different ultrasonic wave propagation directions. Specifically, Ai may represent the divergent ultrasound beams with the first virtual focus A transmitted to the scan target for the i-th time, Bi may represent the divergent ultrasound beams with the second virtual focus B transmitted to the scan target for the i-th time, Ci may represent the divergent ultrasound beams with the third virtual focus C transmitted to the scan target for the i-th time, and Di may represent the divergent ultrasound beams with the fourth virtual focus D transmitted to the scan target for the i-th time; in this case, the transmitting pulse sequences in FIG. 13c may be A1, B1, C1, D1, A2, B2, C2, D2, A3, B3, C3, D3, A4, B4, C4, D4, A5, B5, C5, D5, A6, B6, C6, D6. With such transmission mode, divergent ultrasonic echo signals will not be lost even if the focused ultrasound beams are inserted.

Figure 13D:
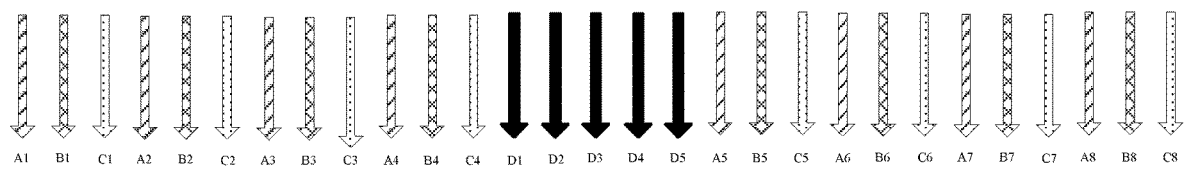
FIG. 13d is a schematic diagram of yet still another transmitting pulse sequences in which divergent ultrasound beams and focused ultrasound beams are alternately transmitted according to the embodiment shown in FIG. 9.

In other embodiments, the transmitting pulse sequences shown in FIG. 13d may also be used to alternately transmit divergent ultrasound beams and focused ultrasound beams to the scan target. In FIG. 13d, the transmissions may be implemented by alternately transmitting the divergent ultrasound beams transmitted continuously for multiple times and the focused ultrasound beams transmitted for multiple time in different ultrasonic wave propagation directions. Specifically, Ai may represent the divergent ultrasound beams with the first virtual focus A transmitted to the scan target for the i-th time, Bi may represent the divergent ultrasound beams with the second virtual focus B transmitted to the scan target for the i-th time, Ci may represent the divergent ultrasound beams with the third virtual focus C transmitted to the scan target for the i-th time, and Di may represent the divergent ultrasound beams with the fourth virtual focus D transmitted to the scan target for the i-th time; in this case, the transmitting pulse sequences in FIG. 13d may be A1, B1, C1, A2, B2, C2, A3, B3, C3, A4, B4, C4, D1, D2, D3, D4, D5, A5, B5, C5, A6, B6, C6, A7, B7, C7, A8, B8, C8. With such transmission mode, divergent ultrasonic echo signals will also not be lost.

FIGS. 13a-13d only illustrate a mode in which the divergent ultrasound beams and the focused ultrasound beams are alternatively transmitted. Other modes may also be adopted to achieve alternate scanning to the scan target by the divergent ultrasound beams and the focused ultrasound beams. For example, the transmitting pulse sequences of the divergent ultrasound beams shown in FIGS. 8a-8d may be applied to FIGS. 13a-13d to form another alternative transmitting pulse sequences of the divergent ultrasound beams and the focused ultrasound beams.

In step S22, the echoes of the divergent ultrasound beams may be received to obtain a group of divergent ultrasonic echo signals when the probe transmits the divergent ultrasound beams to the scan target; and the focused ultrasound may be received to obtain a group of focused ultrasonic echo signals when the probe transmits the focused ultrasound beams to the scan target. The divergent ultrasonic echo signals may be used for ultrasound blood flow imaging, and the focused ultrasonic echo signals may be used for gray-scale imaging.

In step S23, the processor may calculate the blood flow velocity vector information of the scan target (especially a selected target point) based on the divergent ultrasonic echo signals. The processor may obtain the gray value of each pixel of the scan target in the scanning area according to the focused ultrasonic echo signals and generate a grayscale ultrasonic image.

In step S24, the ultrasonic image of the scan target and the blood flow velocity vector information may be displayed simultaneously. As mentioned above, the blood flow velocity vector information can be illustrated in the form of a projection body. The projection body may be an arrow starting from the location of the target point, and the arrow may move with the movement of the target point. The projection body may be a line segment with an arrow end, and the starting point of the line segment is the current position of the target point. When the blood flow velocity vector information and ultrasonic image are displayed synchronously, the scan target changing over time may be shown to the user.

The above-mentioned imaging methods of transmitting focused ultrasound beams and divergent ultrasound beams can better meet the different requirements of grayscale imaging and blood flow imaging; thus it can not only obtain clearer gray-scale images, but also display good blood flow signals more intuitively on the grayscale images.

An ultrasound imaging system may also be provided in the present disclosure, which may include a probe 1, a transmitting circuit 2, a receiving circuit 4, a beam synthesis unit 5, a processor 6 and a display 7.

The probe 1 may include an array of multiple transducers, and all and part of the multiple transducers may transmit ultrasonic waves under the excitation of the transmitting circuit 2. The probe 1 and the transmitting circuit 2 may be used to perform the above step S11; that is, the probe 1 is excited by the transmitting circuit 2 to transmit divergent ultrasound beams that may be used to scan the scan target to the scan target. When the divergent ultrasound beams may be transmitted to the heart of a scan target based on a phased array probe, the scanning area defined by the divergent ultrasound beams can cover the entire heart. The transmitting circuit 2 may control the transmission time delays of the transducers of the probe 1 to form the divergent ultrasound beams with different ultrasonic wave propagation directions (or referred to as different virtual focuses) as described above, which will not be repeated. The probe 1 and the transmitting circuit 2 may also be used to perform the above step S21, that is, alternately transmitting focused ultrasound beams and divergent ultrasound beams to the scan target. The transmitting circuit may control the transmission time delays excited by the transmitting pulses, so that the plurality of transducers may be excited to transmit ultrasonic waves at different times to form the divergent ultrasound beams or focused ultrasonic waves.

The probe 1, the receiving circuit 4, and the beam synthesis unit 5 may be used to perform the above step S12. That is, the probe 1 may receive the echoes of the divergent ultrasound beams from the scan target and convert it into the first electric signals; the receiving circuit 4 may receive the first electric signals; and the beam synthesis unit 5 may perform beam synthesis on the first electric signals to obtain divergent ultrasonic echo signals. The beam synthesis unit 5 can perform beam synthesis based on each pixel in the scanning area of the divergent line or divergent ultrasonic waves. The probe 1, the receiving circuit 4, and the beam synthesis unit 5 may be also used to perform the above step S22. In addition to obtaining divergent ultrasonic echo signals, the probe 1, the receiving circuit 4 and the beam synthesis unit 5 may also receive echoes of the focused ultrasound beams to obtain focused ultrasonic echo signals.

The processor 6 may be used to execute the above steps S13 and S23. After transmitting the divergent ultrasound beams multiple times, the processor 6, based on a corresponding group of divergent ultrasonic echo signals, may calculate the direction and magnitude of the velocity of the selected scan target and generate the blood flow velocity vector information of the target point. For example, the processor 6 can perform related calculations about ultrasound blood flow imaging based on wall filtering or spot tracking. After transmitting the focused ultrasound beams multiple times, the processor 6 may perform grayscale image processing on the obtained focused ultrasonic echo signals to acquire at least a part of the ultrasonic image of the scan target. The processor 6 may also perform grayscale image processing on the obtained divergent ultrasonic echo signals to acquire at least a part of the ultrasonic image of the scan target.

The display 7 may be used to perform the above steps S14 and S24, and synchronously display the ultrasonic image and the blood flow velocity vector information of the target point in the image on the display.

In summary, the ultrasound imaging system and imaging method provided by the present disclosure use divergent ultrasound beams to perform ultrasound blood flow imaging. By means of the divergent ultrasound beams, a larger scanning area may be provided; further, an approximately trapezoidal scanning area may be acquired in cardiac scanning even when a phased array probe is used, thus achieving a high frame rate scan of the entire heart. In the present disclosure, the divergent ultrasound beams and the focused ultrasound beams may be used to perform alternate scanning, resulting in high-quality grayscale ultrasonic images and intuitively displayed vector flow information.

The present disclosure is described with reference to various exemplary embodiments. However, those skilled in the art will recognize that changes and modifications can be made to the exemplary embodiments without departing from the scope of the present disclosure. For example, various operation steps and components used to perform the operation steps can be implemented in different ways according to specific applications or considering any number of cost functions associated with the operation of the system (for example, one or more steps can be deleted, modified or incorporated into other steps).

In addition, as understood by those skilled in the art, the principles herein can be reflected in a computer program product on a computer-readable storage medium, which is pre-loaded with computer-readable program code. Any tangible, non-transitory computer-readable storage medium can be used, including magnetic storage devices (hard disks, floppy disks, etc.), optical storage devices (CD-ROM, DVD, Blue Ray disks, etc.), flash memory and/or the like. These computer program instructions can be loaded on a general-purpose computer, a special-purpose computer, or other programmable data processing equipment to form a machine, so that the instructions executed on the computer or other programmable data processing device can generate a device that realizes a specified function. These computer program instructions can also be stored in a computer-readable memory, which can instruct a computer or other programmable data processing equipment to run in a specific manner, so that the instructions stored in the computer-readable memory can form a piece of fabrication, including a realizing apparatus that is used to realize a designated function. Computer program instructions can also be loaded on a computer or other programmable data processing equipment, thereby executing a series of operating steps on the computer or other programmable equipment to produce a computer-implemented process, so that the instructions executed on the computer or other programmable devices can provide steps for realizing the specified functions.

Although the principles of the present disclosure have been shown in various embodiments, many modifications of structures, arrangements, proportions, elements, materials, and components that are particularly suitable for specific environments and operating requirements can be made without departing from the principles and scope of this disclosure. The above modifications and other changes or amendments will be included in the scope of the present disclosure.

The foregoing Detailed Description has been illustrated with reference to various embodiments. However, those skilled in the art will recognize that various modifications and changes can be made without departing from the scope of this disclosure. Therefore, this disclosure will be in an illustrative rather than restrictive sense, and all these modifications will be included in its scope. Likewise, the advantages of the various embodiments, other advantages, and solutions to problems have been described above. However, benefits, advantages, solutions to problems, and any elements that can produce these, or make them more specific, should not be construed as critical, necessary, or indispensable. The term "including" and any other variants thereof used herein are non-exclusive inclusions. Such a process, method, article or device that includes a list of elements not only includes these elements, but also includes those that are not explicitly listed or are not part of the process, method, system, article or device. In addition, the term "connect" and any other variations thereof used herein refer to physical connection, electrical connection, magnetic connection, optical connection, communication connection, functional connection and/or any other connection.

Those skilled in the art will recognize that many changes can be made to the details of the above-described embodiments without departing from the basic principles of the present disclosure. Therefore, the scope of the present disclosure should be determined according to the following claims.

What is claimed is:

1. An ultrasound blood flow imaging method, comprising:
    transmitting first divergent ultrasound beams corresponding to a first virtual focus to a scan target at least twice, a to-be-scanned region of the scan target being covered by a first scanning area of the first divergent ultrasound beams; and transmitting second divergent ultrasound beams corresponding to a second virtual focus to the scan target at least twice, the to-be-scanned region of the scan target being covered by a second scanning area of the second divergent ultrasound beams;
    receiving echoes of the first divergent ultrasound beams to obtain a group of first divergent ultrasonic echo signals that includes the first divergent ultrasonic echo signals received at least twice; and receiving echoes of the second divergent ultrasound beams to obtain a group of second divergent ultrasonic echo signals that includes the second divergent ultrasonic echo signals received at least twice;
    calculating a first velocity component of a target point in the to-be-scanned region of the scan target in a first direction based on the group of the first divergent ultrasonic echo signals; and calculating a second velocity component of the target point in the to-be-scanned region of the scan target in a second direction based on the group of the second divergent ultrasonic echo signals;
    generating a blood flow velocity vector information of the target point in the to-be-scanned region based on the first velocity component and the second velocity component; and
    displaying the blood flow velocity vector information of the target point in the to-be-scanned region;
    wherein a position of the first virtual focus is different from a position of the second virtual focus, the first scanning area and the second scanning area are at least partially overlapped, and the to-be-scanned region of the scan target is covered by the overlapped scanning area, wherein the overlapped scanning area obtained by overlapping the first scanning area and the second scanning area is a substantially trapezoidal scanning area that covers the to-be-scanned region of the scan target, and a size of the substantially trapezoidal scanning area in a position away from a plane on which a plurality of transducers are arranged is larger than a size of the substantially trapezoidal scanning area in a position close to the plane on which the plurality of transducers are arranged; and
    wherein the plurality of transducers of a probe are excited with a first group of transmission time delays to transmit ultrasonic waves to the scan target to form the first divergent ultrasound beams, wherein ultrasonic waves transmitted by transducers closer to the first virtual focus are transmitted earlier than ultrasonic waves transmitted by transducers far away from the first virtual focus; and the plurality of transducers of the probe are excited with a second group of transmission time delays that is different from the first group of transmission time delays to transmit ultrasonic waves to the scan target to form the second divergent ultrasound beams, wherein ultrasonic waves transmitted by transducers closer to the second virtual focus are transmitted earlier than ultrasonic waves transmitted by transducers far away from the second virtual focus.

2. The method according to claim 1, wherein the first direction is a direction of a connecting line that connects the first virtual focus with the target point in the to-be-scanned region, and the second direction is a direction of a connecting line that connects the second virtual focus with the target point in the to-be-scanned region.

3. The method according to claim 1, wherein the first divergent ultrasound beams corresponding to the first virtual focus and the second divergent ultrasound beams corresponding to the second virtual focus are alternately transmitted to the scan target.

4. The method according to claim 1, further comprising:
    obtaining an ultrasonic image of at least a part of the to-be-scanned region of the scan target; and
    superposing the blood flow velocity vector information of the target point in the to-be-scanned region on the ultrasonic image, and synchronously displaying the ultrasonic image and the blood flow velocity vector information of the target point in the to-be-scanned region;

wherein according to the group of the first divergent ultrasonic echo signals and/or the second divergent ultrasonic echo signals, gray information of the to-be-scanned region of the scan target is calculated to generate the ultrasonic image; or focused ultrasound beams are transmitted to the scan target, focused ultrasonic echo signals are obtained based on the transmitted focused ultrasound beams, and gray information of the to-be-scanned region of the scan target is calculated to generate the ultrasonic image.

5. The method according to claim 4, wherein the first divergent ultrasound beams, the second divergent ultrasound beams and the focused ultrasound beams are alternately transmitted to the scan target.

6. The method according to claim 4, wherein the first divergent ultrasound beams, the second divergent ultrasound beams and the focused ultrasound beams are alternately transmitted to the scan target one after another; or the first divergent ultrasound beams and the second divergent ultrasound beams are alternately transmitted, and the focused ultrasound beams are inserted one or more times between the first divergent ultrasound beams and the second divergent ultrasound beams that are alternately transmitted a plurality of times; or the first divergent ultrasound beams and the second divergent ultrasound beams are alternately transmitted, and the focused ultrasound beams are transmitted a plurality of times in a time-sharing manner between the first divergent ultrasound beams and the second divergent ultrasound beams that are alternately transmitted a plurality of times.

7. The method according to claim 1, wherein the first divergent ultrasound beams comprise a plurality of first divergent lines that pass through the first virtual focus, and the second divergent ultrasound beams comprise a plurality of second divergent lines that pass through the second virtual focus;

receiving the echoes of the first divergent ultrasound beams to obtain the group of first divergent ultrasonic echo signals comprises: receiving the echoes of the first divergent ultrasound beams to obtain first electric signals, and performing beam synthesis on the first electric signals along the plurality of first divergent lines to obtain the group of first divergent ultrasonic echo signals; and receiving the echoes of the second divergent ultrasound beams to obtain the group of second divergent ultrasonic echo signals comprises: receiving the echoes of the second divergent ultrasound beams to obtain second electric signals, and performing beam synthesis on the second electric signals along the plurality of second divergent lines to obtain the group of second divergent ultrasonic echo signals.

8. The method according to claim 1, wherein displaying the blood flow velocity vector information of the target point in the to-be-scanned region comprises:

dynamically displaying the blood flow velocity vector information of the target point through a motion trajectory of a moving projection body; or statically displaying the blood flow velocity vector information of the target point through a magnitude and direction of a velocity indicator marked at the target point.

9. An ultrasound blood flow imaging method, comprising:

exciting a probe by a transmitting circuit to transmit divergent ultrasound beams corresponding to a virtual focus to a to-be-scanned region of a scan target that is covered by a scanning area of the divergent ultrasound beams;

receiving echoes of the divergent ultrasound beams by the probe to obtain first electric signals, receiving the first electric signals by a receiving circuit, and performing beam synthesis on the first electric signals by a beamformer to obtain a group of divergent ultrasonic echo signals;

calculating a direction and magnitude of a velocity of a target point in the to-be-scanned region of the scan target by a processor based on the group of divergent ultrasonic echo signals to generate a blood flow velocity vector information of the target point in the to-be-scanned region; and displaying the blood flow velocity vector information of the target point in the to-be-scanned region on a display, wherein a plurality of transducers of the probe are excited with a first group of transmission time delays to transmit ultrasonic waves to the scan target to form the divergent ultrasound beams, wherein an ultrasonic wave transmitted by a transducer closer to the virtual focus is transmitted earlier than an ultrasonic wave transmitted by a transducer far away from the virtual focus, wherein the divergent ultrasound beams comprise first divergent ultrasound beams and second divergent ultrasound beams that are transmitted in different ultrasonic waves propagation directions, and the target point in the to-be-scanned region is located in a scanning area scanned by both the first divergent ultrasound beams and the second divergent ultrasound beams, wherein the scanning area scanned by both the first divergent ultrasound beams and the second divergent ultrasound beams is a substantially trapezoidal scanning area that covers the to-be-scanned region of the scan target, and a size of the substantially trapezoidal scanning area in a position away from a plane on which the plurality of transducers are arranged is larger than a size of the substantially trapezoidal scanning area in a position close to the plane on which the plurality of transducers are arranged.

10. The method according to claim 9, wherein calculating the direction and magnitude of the velocity of the target point in the to-be-scanned region of the scan target by the processor based on the group of divergent ultrasonic echo signals to generate the blood flow velocity vector information of the target point in the to-be-scanned region comprises:

according to first divergent ultrasonic echo signals obtained by the transmitted first divergent ultrasound beams, calculating a velocity component of the target point in the to-be-scanned region of the scan target in a first direction by the processor;

according to second divergent ultrasonic echo signals obtained by the transmitted second divergent ultrasound beams, calculating a velocity component of the target point in the to-be-scanned region of the scan target in a second direction by the processor; and synthesizing the velocity component in the first direction and the velocity component in the second direction by the processor to obtain the blood flow velocity vector information of the target point in the to-be-scanned region.

11. The method according to claim 9, wherein performing beam synthesis by the beamformer to obtain the group of divergent ultrasonic echo signals comprises: performing beam synthesis based on divergent lines of the divergent ultrasound beams or based on pixels in the scanning area of the divergent ultrasound beams to obtain the group of divergent ultrasonic echo signals.

12. The method according to claim 9, wherein displaying the blood flow velocity vector information of the target point in the to-be-scanned region on the display comprises: displaying the blood flow velocity vector information of the target point in the to-be-scanned region as a moving projection body on the display, wherein a position of the projection body is dynamically updated to illustrate a motion trajectory of the projection body.

13. An ultrasound imaging system, comprising:
- a probe, comprising a plurality of transducers and configured to transmit divergent ultrasound beams corresponding to a virtual focus and receive echoes of the divergent ultrasound beams to obtain first electric signals;
- a transmitting circuit, configured to excite the probe to transmit the divergent ultrasound beams to a scan target to scan the scan target, wherein an ultrasonic wave transmitted by a transducer closer to the virtual focus is transmitted earlier than an ultrasonic wave transmitted by a transducer far away from the virtual focus;
- a receiving circuit and a beamformer, configured to receive and process the first electric signals to obtain divergent ultrasonic echo signals;
- a processor, configured to obtain a blood flow velocity vector information of the scan target according to the divergent ultrasonic echo signals; and
- a display, configured to display the blood flow velocity vector information of the scan target,
- wherein the transmitting circuit is further configured to excite the probe to transmit a plurality of divergent ultrasound beams having different virtual focuses to the scan target;
- the receiving circuit and the beamformer are further configured to obtain multiple groups of divergent ultrasonic echo signals based on the corresponding divergent ultrasound beams having different virtual focuses; and
- the processor is further configured to obtain a plurality of velocity components according to the multiple groups of divergent ultrasonic echo signals and synthesize the plurality of velocity components to obtain the blood flow velocity vector information of the scan target,
- wherein a scanning area scanned by the plurality of divergent ultrasound beams having different virtual focuses is a substantially trapezoidal scanning area, and a size of the substantially trapezoidal scanning area in a position away from a plane on which the plurality of transducers are arranged is larger than a size of the substantially trapezoidal scanning area in a position close to the plane on which the plurality of transducers are arranged.

14. The system according to claim 13, wherein
the processor is further configured to obtain an ultrasonic image of the scan target according to the multiple groups of divergent ultrasonic echo signals, and the display is further configured to synchronously display the ultrasonic image and the blood flow velocity vector information.

15. The system according to claim 13, wherein
the transmitting circuit is further configured to excite the probe to transmit focused ultrasound beams to the scan target, wherein the focused ultrasound beams and the divergent ultrasound beams are alternately transmitted;
the probe is further configured to receive echoes of the focused ultrasound beams from the scan target to obtain second electric signals, and the receiving circuit and the beamformer are further configured to receive and process the second electric signals to obtain focused ultrasonic echo signals;
the processor is further configured to obtain an ultrasonic image of the scan target according to the focused ultrasonic echo signals; and
the display is further configured to synchronously display the ultrasonic image and the blood flow velocity vector information.

* * * * *